(12) United States Patent
Avisar et al.

(10) Patent No.: US 12,419,699 B2
(45) Date of Patent: Sep. 23, 2025

(54) SYSTEM AND METHOD FOR AUGMENTED REALITY SPINE SURGERY

(71) Applicant: Surgical Theater, Inc., Los Angeles, CA (US)

(72) Inventors: Mordechai Avisar, Highland Heights, OH (US); Alon Yakob Geri, Orange Village, OH (US); Robert Louis, Newport Beach, CA (US)

(*) Notice: Subject to any disclaimer, the term of this patent is extended or adjusted under 35 U.S.C. 154(b) by 995 days.

(21) Appl. No.: 17/397,157

(22) Filed: Aug. 9, 2021

(65) Prior Publication Data

US 2022/0039881 A1 Feb. 10, 2022

Related U.S. Application Data

(60) Provisional application No. 63/062,921, filed on Aug. 7, 2020, provisional application No. 63/068,079, filed on Aug. 20, 2020, provisional application No. 63/116,457, filed on Nov. 20, 2020.

(51) Int. Cl.
*A61B 34/00* (2016.01)
*A61B 34/10* (2016.01)
*A61B 34/20* (2016.01)
*G06F 3/01* (2006.01)

(52) U.S. Cl.
CPC .............. *A61B 34/25* (2016.02); *A61B 34/10* (2016.02); *A61B 34/20* (2016.02); *G06F 3/011* (2013.01); *A61B 2034/102* (2016.02); *A61B 2034/105* (2016.02); *A61B 2034/2068* (2016.02); *A61B 2034/256* (2016.02)

(58) Field of Classification Search
None
See application file for complete search history.

(56) References Cited

U.S. PATENT DOCUMENTS

| | | | | |
|---|---|---|---|---|
| 2017/0312031 A1* | 11/2017 | Amanatullah | ......... | A61B 34/10 |
| 2017/0312032 A1* | 11/2017 | Amanatullah | ......... | G09B 23/30 |
| 2017/0367771 A1* | 12/2017 | Tako | ...................... | G16H 20/40 |
| 2020/0246074 A1* | 8/2020 | Lang | .................... | A61B 17/155 |
| 2021/0074183 A1* | 3/2021 | Van Flute | .............. | A61B 34/10 |

\* cited by examiner

*Primary Examiner* — Martin Mushambo

(57) ABSTRACT

A system and method for providing an imaging system comprising an image generator and a MD6DM model, for creating a synchronized augmented reality view of a subject. In particular, the imaging system enables augmenting and overlaying the MD6DM model over top of a corresponding physical model. Moreover, the imaging system anchors the MD6DM model to the physical model and synchronizes the two, such that a new image is created and overplayed over top of the physical model according to movement around the model, such as using a physical probe. This is accomplished by streaming the image generator directly to an HMD, tracking a position and location of the HMD, and adjusting the image generator based on the tracked movement. Thus, a dependency is created between the virtual model and the physical model. Guides can be provided to the user to enable the user to simulate and practice placing a virtual accessory, such as a model of an implantable screw, into a desired location in the physical model.

23 Claims, 13 Drawing Sheets

SYSTEM AND METHOD FOR AUGMENTED REALITY SPINE SURGERY

CROSS-REFERENCES TO RELATED APPLICATIONS

This application claims the benefit of U.S. provisional application Ser. No. 63/062,921 filed on Aug. 7, 2020, U.S. provisional application Ser. No. 63/068,079 filed on Aug. 20, 2020, and U.S. provisional application Ser. No. 63/116,457 filed on Nov. 20, 2020, all incorporated herein by reference.

BACKGROUND

Surgical procedures may often be complex and time sensitive and vary in scope from one patient to another. For example, in the case of spine surgery, the point of repair may vary in terms or procedural requirements depending on the exact location, size, and so on. Therefore, the efficiency of the procedure is highly critical and detailed planning based on the patient specific local geometry and physical properties of the area on which surgery is being performed is fundamental. To achieve a new level of pre-surgery preparation, 3D CT and MRI images are being increasingly utilized. However, those images offer only minor benefits, standing alone, for surgery rehearsal. Moreover, existing techniques for studying a patient's specific anatomy prior to or during surgery may be invasive to the patient.

SUMMARY

Provided are a plurality of example embodiments, including, but not limited to, a method for using a computer system for rendering an interactive augmented view of a physical model representing an anatomical feature and virtual accessory model of an implantable surgical accessary, said method comprising the steps of:
    storing data representing the implantable surgical accessory in a database;
    providing a physical probe configured for use by a user to interact with the physical model;
    the computer system being configured for generating the virtual accessory model of the implantable surgical accessory utilizing the data representing the implantable surgical accessory;
    the computer system being configured for determining a direction of view of the user;
    the computer system being configured for tracking a position of the physical probe about the physical model;
    the computer system being configured for generating an image of the physical model based on the determined direction of view of the user;
    the computer system being configured for generating an image of the surgical probe based on the tracked position of the physical probe; and
    the computer system being configured for generating and displaying an augmented reality view to the user, said augmented reality view showing realistic interaction of the virtual accessory model with the generated image of the physical probe and the generated image of the physical model such that the user can realistically manipulate the virtual accessory model based on user interactions with the physical probe about the physical model.

Also provided is a method for using a computer system for rendering an interactive augmented view of a physical model representing an anatomical feature and virtual accessory model of a commercially available implantable surgical accessary, said method comprising the steps of:
    storing data representing the implantable surgical accessory in a database;
    providing a physical probe configured for use by a user to interact with the physical model;
    the computer system being configured for generating the virtual accessory model of the implantable surgical accessory utilizing the data representing the implantable surgical accessory;
    the computer system being configured for determining a direction of view of the user;
    the computer system being configured for tracking a position of the physical probe about the physical model;
    the computer system being configured for generating an image of the physical model based on the determined direction of view of the user;
    the computer system being configured for generating an image of the surgical probe based on the tracked position of the physical probe;
    the computer system being configured for generating and displaying an augmented reality view to the user, said augmented reality view showing realistic interaction of the virtual accessory model with the generated image of the physical probe and the generated image of the physical model such that the user can realistically manipulate the virtual accessory model based on user interactions with the physical probe about the physical model; and
    the computer system being configured for displaying, in the augmented reality view, one or more guide markers on the image of the physical model to guide the user in maneuvering the physical probe to a desired placement of the virtual accessory model with respect to the physical model.

Further provided is the above method further comprising the steps of:
    performing a proximity test on the physical probe to detect a distance between the physical probe and a predetermined threshold level of a desired location of the virtual accessory; and
    utilizing said one or more guide markers to further refine guiding the user to position the virtual accessory into the desired location based on said proximity test.

Further provided is a method for using a computer system for rendering an interactive augmented view of a physical model representing an anatomical feature and virtual accessory model of a commercially available implantable surgical accessary, said method comprising the steps of:
    storing data representing the implantable surgical accessory in a database;
    providing a physical probe configured for use by a user to interact with the physical model;
    the computer system being configured for generating the virtual accessory model of the implantable surgical accessory utilizing the data representing the implantable surgical accessory;
    the computer system being configured for determining a direction of view of the user;
    the computer system being configured for tracking a position of the physical probe about the physical model;

the computer system being configured for generating a virtual model of the physical model based on the determined direction of view of the user and desired features of the virtual model of the physical model stored in the database;

the computer system being configured for generating a virtual model of the surgical probe based on the tracked position of the physical probe and desired features of the virtual model of the physical probe stored in the database;

the computer system being configured for generating and displaying an augmented reality view to the user, said augmented reality view showing realistic interaction of the virtual accessory model with the virtual model of the physical probe and the virtual model of the physical model such that the user can realistically manipulate the virtual accessory model based on user interactions with the physical probe about the physical model;

the computer system being configured for displaying, in the augmented reality view, one or more guide markers on the virtual model of the physical model to guide the user in maneuvering the physical probe to a desired placement of the virtual accessory model with respect to the virtual model of the physical model;

performing a proximity test on the physical probe to detect a distance between the virtual model of the physical probe and a predetermined threshold level of a desired location of the virtual accessory; and utilizing said one or more guide markers to further refine guiding the user to position the virtual accessory into the desired location on the virtual model of the physical model based on said proximity test.

Still further provided is method for using a computer system for rendering an interactive augmented view of a physical model including at least part of a skeleton and a virtual screw model of a commercially available implantable screw, said method comprising the steps of:

storing data representing the implantable screw in a database;

providing a physical probe configured for use by a user to interact with the physical model;

the computer system being configured for generating the virtual screw model of the implantable screw utilizing the data representing the implantable screw;

the computer system being configured for determining a direction of view of the user;

the computer system being configured for tracking a position of the physical probe about the physical model;

the computer system being configured for generating an image of the physical model based on the determined direction of view of the user;

the computer system being configured for generating an image of the surgical probe based on the tracked position of the physical probe;

the computer system being configured for generating and displaying an augmented reality view to the user, said augmented reality view showing realistic interaction of the screw model with the generated image of the physical probe and the generated image of the physical model such that the user can realistically manipulate the screw model based on user interactions with the physical probe about the physical model to interact with the part of the skeleton; and the computer system being configured for displaying, in the augmented reality view, one or more guide markers on the image of the physical model to guide the user in maneuvering the physical probe to a desired placement of the screw model with respect to the part of the skeleton.

Still further provided is a system including a computer system for performing any of the above methods or subsets or enhancements thereof.

Also provided are additional example embodiments, some, but not all of which, are described hereinbelow in more detail

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

Figure 1:
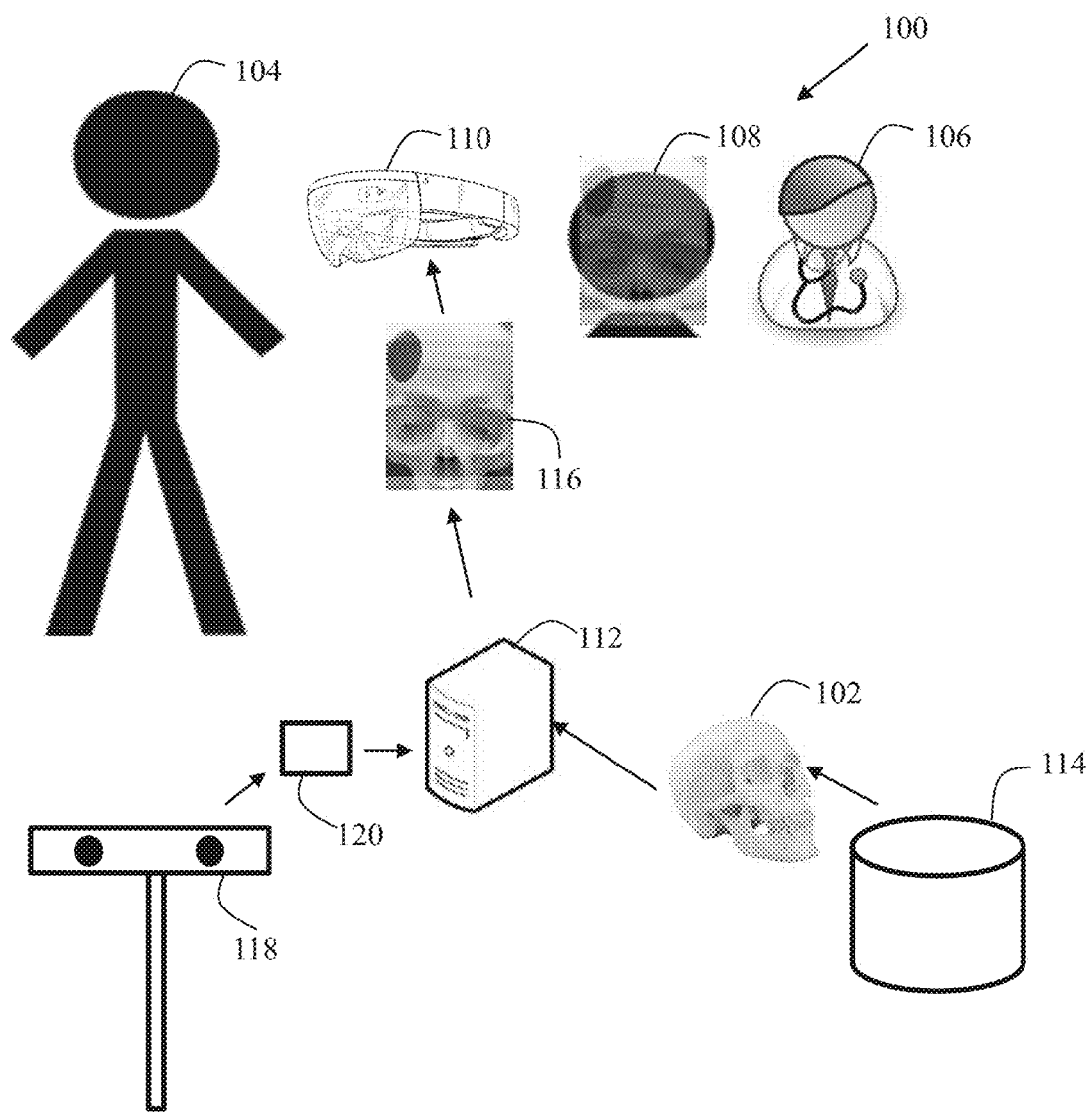
FIG. 1 illustrates an example system for augmented reality spine surgery.

The following acronyms and definitions will aid in understanding the detailed description:

AR—Augmented Reality—A live view of a physical, real-world environment whose elements have been enhanced by computer generated sensory elements such as sound, video, or graphics.

VR—Virtual Reality—A 3Dimensional computer generated environment which can be explored and interacted with by a person in varying degrees.

HMD—Head Mounted Display refers to a headset which can be used in AR or VR environments. It may be wired or wireless. It may also include one or more add-ons such as headphones, microphone, HD camera, infrared camera, hand trackers, positional trackers etc.

Controller—A device which includes buttons and a direction controller. It may be wired or wireless. Examples of this device are Xbox gamepad, PlayStation gamepad, Oculus touch, etc.

SNAP Model—A SNAP case refers to a 3D texture or 3D objects created using one or more scans of a patient (CT, MR, fMR, DTI, etc.) in DICOM file format. It also includes different presets of segmentation for filtering specific ranges and coloring others in the 3D texture. It may also include 3D objects placed in the scene including 3D shapes to mark specific points or anatomy of interest, 3D Labels, 3D Measurement markers, 3D Arrows for guidance, and 3D surgical tools. Surgical tools and devices have been modeled for education and patient specific rehearsal, particularly for appropriately sizing aneurysm clips.

Avatar—An avatar represents a user inside the virtual environment.

MD6DM—Multi Dimension full spherical virtual reality, 6 Degrees of Freedom Model. It provides a graphical simulation environment which enables the physician to experience, plan, perform, and navigate the intervention in full spherical virtual reality environment.

A surgery rehearsal and preparation tool previously described in U.S. Pat. No. 8,311,791, incorporated in this application by reference, has been developed to convert static CT and MRI medical images into dynamic and interactive multi-dimensional full spherical virtual reality, six (6) degrees of freedom models ("MD6DM") based on a prebuilt SNAP model that can be used by physicians to simulate medical procedures in real time. The MD6DM provides a graphical simulation environment which enables the physician to experience, plan, perform, and navigate the intervention in full spherical virtual reality environment. In particular, the MD6DM gives the surgeon the capability to navigate using a unique multidimensional model, built from traditional two-dimensional patient medical scans, that gives spherical virtual reality 6 degrees of freedom (i.e. linear; x, y, z, and angular, yaw, pitch, roll) in the entire volumetric spherical virtual reality model.

The MD6DM is rendered in real time by an image generator using a SNAP model built from the patient's own data set of medical images including CT, MM, DTI etc., and is patient specific, such as a SNAP computer previously described in U.S. Pat. No. 8,311,791, incorporated herein by reference. A representative brain model, such as Atlas data, can be integrated to create a partially patient specific model if the surgeon so desires. The model gives a 360° spherical view from any point on the MD6DM. Using the MD6DM, the viewer is positioned virtually inside the anatomy and can look and observe both anatomical and pathological structures as if he were standing inside the patient's body. The viewer can look up, down, over the shoulders etc., and will see native structures in relation to each other, exactly as they are found in the patient. Spatial relationships between internal structures are preserved and can be appreciated using the MD6DM.

The algorithm of the MD6DM rendered by the image generator takes the medical image information and builds it into a spherical model, a complete continuous real time model that can be viewed from any angle while "flying" inside the anatomical structure. In particular, after the CT, MRI, etc. takes a real organism and deconstructs it into hundreds of thin slices built from thousands of points, the MD6DM reverts it to a 3D model by representing a 360° view of each of those points from both the inside and outside.

Described herein is an imaging system, leveraging an image generator and a MD6DM model, for creating a synchronized augmented reality view of a subject. In particular, the imaging system enables augmenting and overlaying the MD6DM model over top of a corresponding physical model. Moreover, the imaging system anchors the MD6DM model to the physical model and synchronizes the two, such that a new image is created and overplayed over top of the physical model according to movement around the model. This is accomplished by streaming the image generator directly to an HMD, tracking a position and location of the HMD, and adjusting the image generator based on the tracked movement. Thus, a dependency is created between the virtual model and the physical model.

By creating such a dependency and tying or anchoring a virtual model to a physical model, and then adjusting an image overplayed on top of the physical model based on movement with respect to the physical model, a HMD is able to receive a synchronized augmented reality view of the physical model regardless of where a user of the HDM is positioned with respect to the physical model, thus offering the user an improved perspective of the physical model. As a result of anchoring the virtual model to the physical model, the visual model is not separated from the physical model. In other words, if a user of the HMD turns his head and looks away from the physical model, the user will no longer see the virtual model either. Only when the user returns focus to the physical model will the user again see the virtual model, overlayed and synchronized as appropriate. Thus, a user may be presented with the augmented view of a main physical object while still providing the user with the freedom and flexibility to maneuver and interact with secondary physical objects within proximity of the main physical object without interfering with the user's view of or interaction with the secondary objects.

It should be appreciated that although reference is made to anchoring or tying a virtual model to a physical model, the virtual model may be anchored to a physical location, rather than to a physical object, and it is understood that the physical object's position does not move during the augmented reality viewing of the physical object.

It should be appreciated that although the examples described herein may refer in general to medical applications and specifically to virtual models or images of a patient's anatomy augmented and synchronized with a corresponding patient's physical body for the purpose of performing spine surgery, the imaging system may similarly be used to synchronize and augment a virtual model or image of any virtual object with a corresponding physical object.

FIG. 1 illustrates a system 100 for augmenting and synchronizing a virtual model 102 with a physical model 104. In particular, the system 100 enables a user 106, such as a physician, to view an augmented realty view 108 of the physical model 104 from any perspective of the physical model 104. In other words, the user 106 may walk around the physical model 104 and view the physical model 104 from any side, angle, or perspective, and to have the synchronized corresponding view of the virtual model 102 overlayed on top of the physical model 104 in order to form the augmented realty view 108. And, if the user 106 turns away from the physical model 104 such that the physical model 104 is no longer within a current view or line of sight, the virtual model 102 similarly is also eliminated from the current view or line of sight.

The virtual model(s) 102 may provide additional biological features for adding to the physical model 104, such as by providing virtual models of internal organs and/or musculature to a physical model of a skeleton, for example. Either or both the virtual model(s) 102 and the physical model 104 may be generic models or models based on the physical biological characteristic of an actual patient as determined by various imaging scanning techniques. The virtual model(s) 102 might alternatively, or additionally, include models of various tools, implants, or other physical entities.

The system 100 includes an augmented reality head mounted display ("HMD") 110 for providing the user 106 with augmented realty view 108 including a live real life visual of the physical model 104 in combination with additionally integrated content, such as the virtual model 102. For example, the system 100 includes an AR synchronization computer 112 for retrieving a virtual model 102 such as a SNAP model, from a virtual model database 114, for rendering a virtual image 116 from the virtual model 102, and for providing the virtual image 116 to the HMD 110. In one example, the AR synchronization computer 112 includes an image generator (not shown) for rendering the virtual image 116 from the virtual model 102. In another example, the image generator is specific to a virtual model 102 and is included with the virtual model 102 retrieved from the virtual model database 114.

It should be appreciated that although the AR synchronization computer 112 is depicted as being external to the HMD 110, in one example, the AR synchronization computer 112 may be incorporated into the HMD 110. This provides for a single integrated solution for receiving and processing a virtual model 102 so that the HMD 110 may provide the user with the augmented reality view 108 as described. In such an example, the virtual model 102, or image generator for the virtual model 102, is streamed directly to the HMD 110.

The AR synchronization computer 112, in combination with the HMD 110, is configured to tie or anchor the virtual model 102 to the physical model 104 and to synchronize the virtual model 102 with and overlay it on top of the live real life visual of the physical model 104 in order to create the augmented realty view 108 of the physical model 104 via the HMD 110. In order to facilitate anchoring and synchronization, the AR synchronization computer 112 is configured to communicate with a navigation system 118. In particular, the AR synchronization computer 112 is configured to receive synchronization and navigation data 120 from the navigation system 118 and to register the HMD 110 with the navigation system 118 using the received synchronization and navigation data 120. In other words, the synchronization and navigation data 120 from the navigation system 118 serves as a physical frame of reference for the AR synchronization computer 112. This enables the AR synchronization computer 112 to tie the virtual model 102 to the physical model 104 by using the synchronization and navigation data 120, or the navigation system reference frame, as the anchor for the virtual model 102. Once anchored, the AR synchronization computer 112 is able to generate the appropriate virtual image 116 depending on tracked movement of the HMD 110 via the navigation system 118.

Figure 2:
FIG. 2 illustrates an example system for augmented reality spine surgery.

FIG. 2 illustrates in more detail how the AR synchronization computer 112 interacts with the navigation system 118 in order to synchronize and overlay the virtual model 102 with the physical model 104, as described in FIG. 1. More specifically, a reference array of markers 202 is positioned near a physical model 204 in order to serve as a reference point for registering the physical model 204. By further registering reference points of a probe or surgical tool 206, the navigation system enables tracking of the probe 206 with respect to the physical model 204.

A headset reference array of markers 208 are positioned on a HMD 210 to further enable registration and tracking of the HMD 210 with respect to the physical model 204. Tracking a unicorn-type pointer 212 positioned on the front of the HMD 210 enables more accurate determination of the direction and angle of view of the HMD 210. Thus, the combination of tracking both the probe 206 and the HMD 210 with respect to the reference array of markers 202 positioned near a physical model 204 creates a unique environment within which a virtual model (not shown) may be displayed to a user via the HMD and synchronized with the physical model 204 such as to enable simultaneous interaction with both the virtual model and the physical model 204.

In order to enable a virtual model to be overplayed and properly synchronized with the physical model 204 so that a user may effectively interact with the virtual model in augmented reality, the virtual model is first aligned with the physical model 204. To facilitate alignment, the virtual model includes a virtual representation of the reference array of markers 208 and is positioned virtually, next to the virtual model identical to the position of the reference array of markers 208 with respect to the physical model 204. Initial alignment is then performed by visually lining up the markers of the reference array 208 with the corresponding virtual reference array markers in the virtual model. This can be performed, for example, using an administrative or setup mode of the system prior to engaging or interacting with the models. In one example, the initial alignment or setup may be performed automatically by the AR synchronization computer 112.

Figure 3:
FIG. 3 illustrates an example system for augmented reality spine surgery.

Once properly aligned, a user may view the physical model 204 via the HMD 210 while simultaneously and in real time view a synchronized virtual model overlayed on top of the physical model 204 in one integrated augmented view 300, as illustrated in FIG. 3. In one example, the integrated augmented view 300 may also include a virtual probe 302 that is synchronized and overlayed with a physical probe. This enables a user to further interact with the integrated augmented view 300 in manners which may otherwise not be possible with a physical probe alone.

Figure 4:
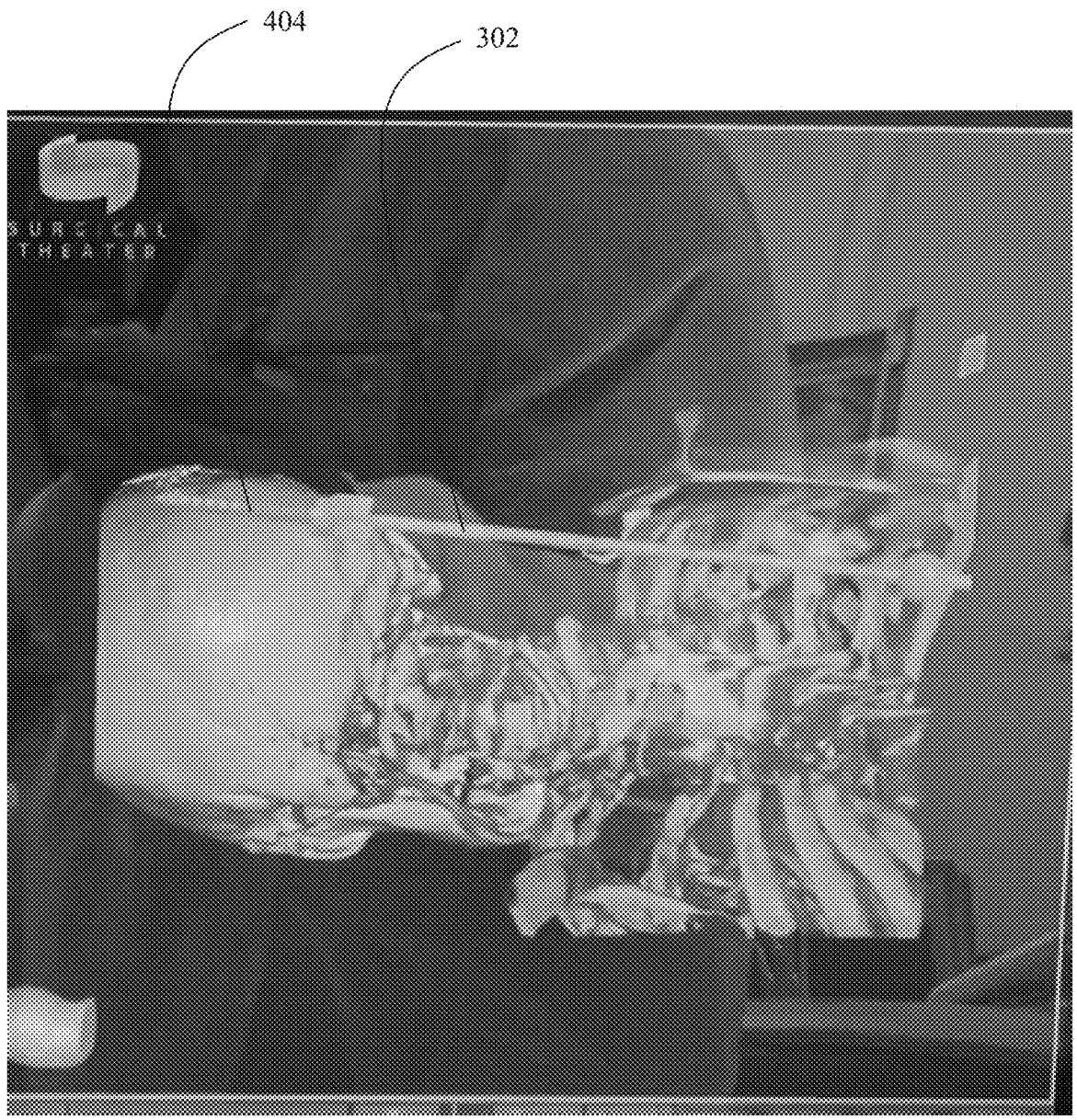
FIG. 4 illustrates an example system for augmented reality spine surgery.

In one example, as illustrated in FIG. 4, a virtual screw 404 may be positioned at the end of the virtual probe 302 in order to allow a user to simulate or practice inserting the virtual screw 404 within the virtual model as part of a simulation or an actual medical procedure. A virtual screw 404 is modeled based on a physical screw. For example, data such as 2D or 3D models and renderings of a screw may be retrieved from a databases, such as a third party provider of such screws such that the virtual screw represents an actual surgical screw for use in medical procedures, and the converted to into a virtual reality or augmented reality 360 degree model for interaction and simulation within the system 100. In one example, data representative of a screw is received in a STEP file format and converted into an OBJ file format. In one example, the conversion of the screw into a VR/AR model includes automatically resizing and scaling the model screw such that the virtual screw 404 has similar properties and dimensions relative to the virtual model.

It should be appreciated that although specific reference is made herein to a screw, any similar type of an actual mechanical or physical accessory for surgical placement or use may be modeled and associated with the virtual probe 302 for surgical procedure simulation, training, and preparation, such that a virtual accessory model representing the actual mechanical or physical accessory are provided for use in the simulation or actual procedure.

Figure 5:
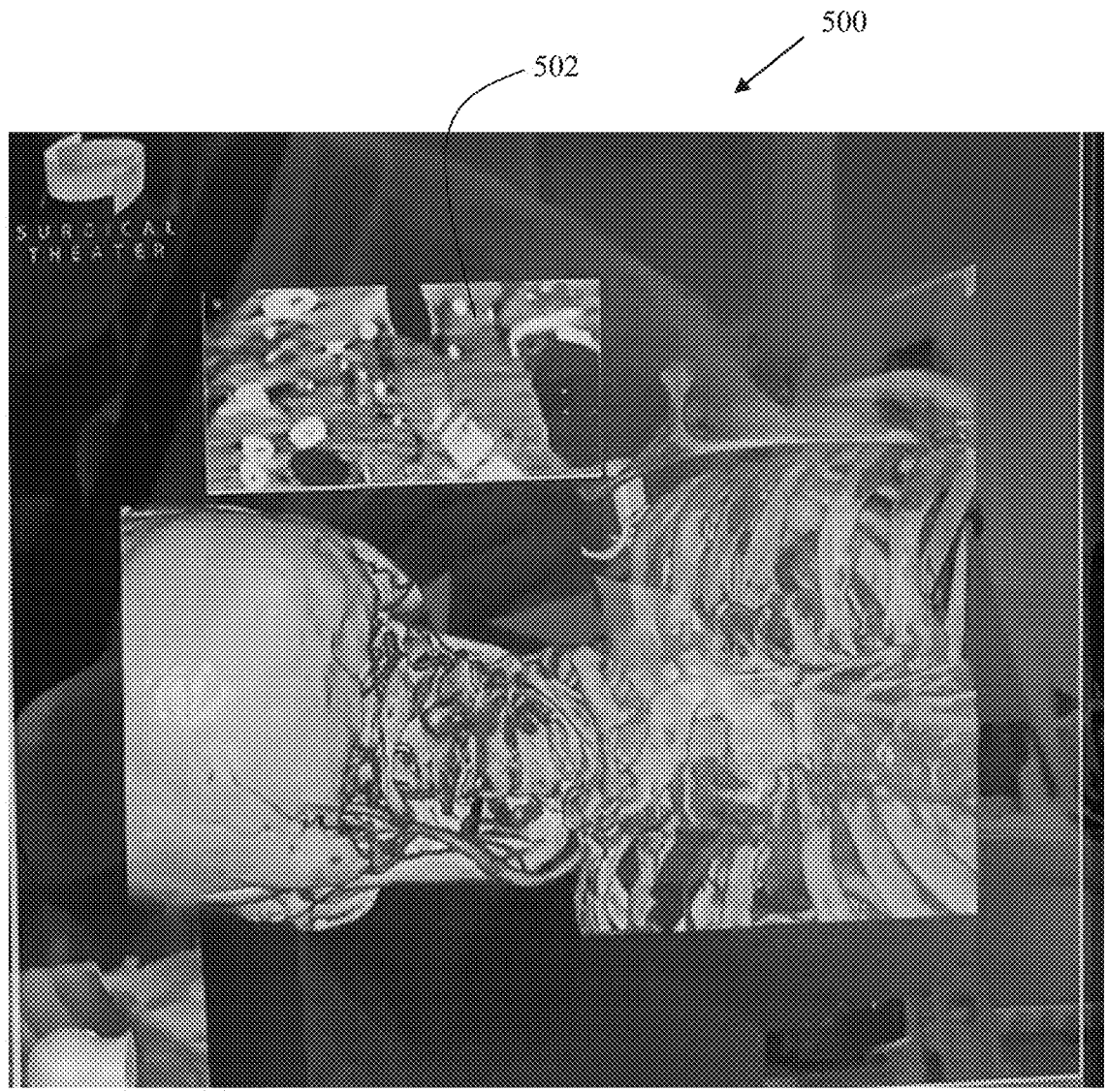
FIG. 5 illustrates an example system for augmented reality spine surgery

In one example, as illustrated in FIG. 5, additional content, such as a DICOM image 502, may be injected into and displayed in an integrated augmented view 500 for the user to further interact with. For example, while viewing and interacting with the integrated augmented view 500, a user may look up or to a side in order to reveal the additional content 502 which may assist the user with the interaction or a surgical procedure, for example. The DICOM image 502 is also synchronized with the tracking data such that movement of the probe and the HMD results in the DICOM image being appropriately updated, rotated, and repositioned as needed.

Figure 8:
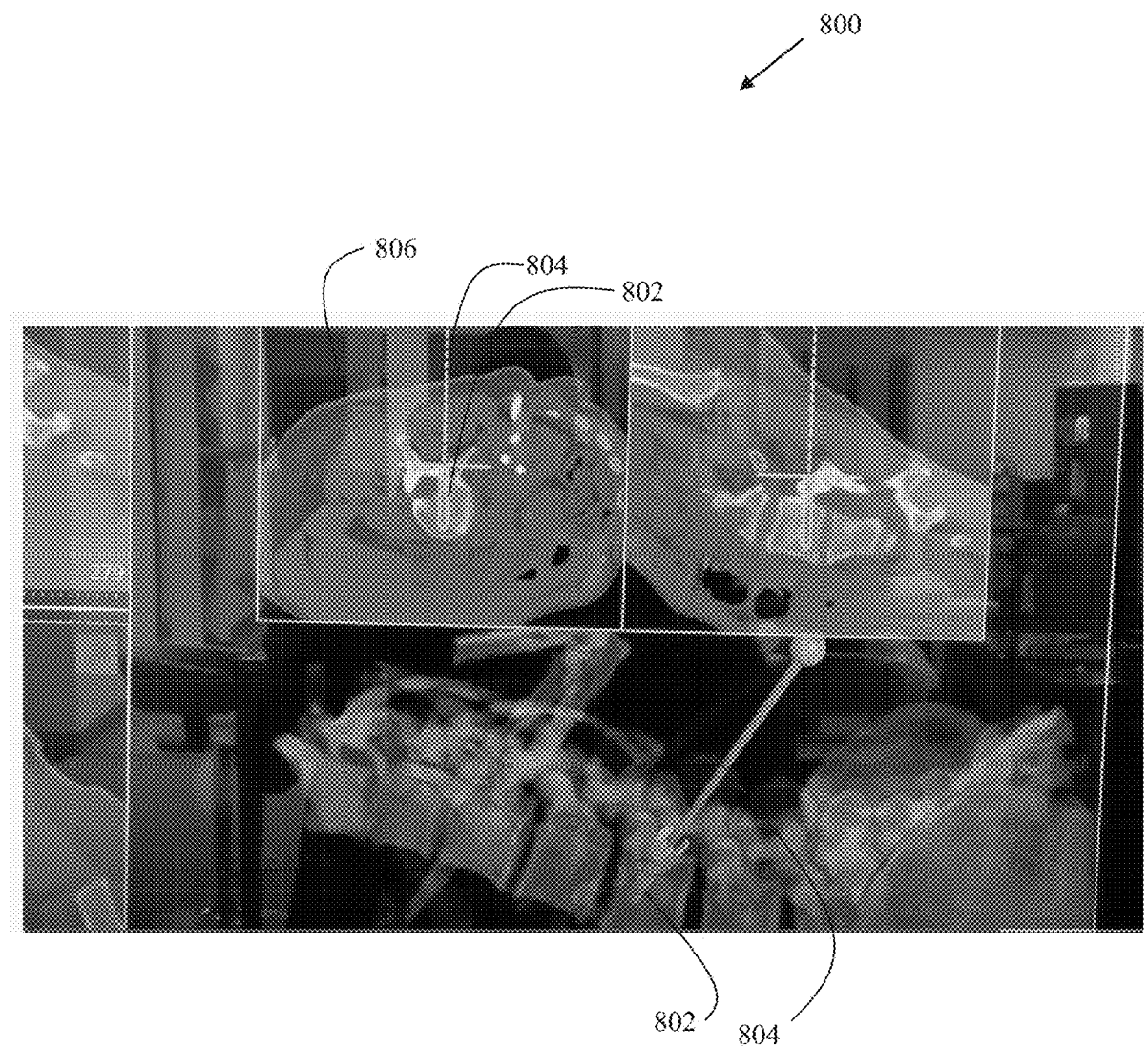
FIG. 8 illustrates an example system for augmented reality spine surgery.

In one example, as illustrated in FIG. 8, a simulation of a virtual screw 802 positioned at the tip of a virtual probe 804 is overplayed on top of the DICOM image 806 injected into and displayed in an integrated augmented view. As a user moves a physical probe with respect to a physical model, or as the user adjusts a view such that the angle of view or position of a HMD with respect to the physical model changes, the movement of the virtual screw 802 as well as the virtual probe 804 is synchronized and updated accordingly. In other words, when a user moves a physical probe near a physical model such as an anatomy of a patient, the user experiences, via an augmented view of the anatomy, a virtual model overlaid on the physical model, virtual probe holding a model virtual screw in or near the virtual model in sync with the physical probe, a DICOM of the same anatomy displayed about (or near) the virtual model, and a representation of the probe holding the screw displayed on top of the DICOM, with all three being synchronized in movement, meaning that the position of the virtual probe and the screw, both on the virtual model and over the DICOM, is synchronized and updated automatically to correspond to movement of the physical probe.

In order to properly synchronize the virtual screw on the DICOM, which is a 2D image, a trajectory view of the DICOM is generated. In particular, the DICOM is displayed in a plane that is perpendicular to the probe so that the DICOM may be visualized from the angle of view of the probe.

In one example, a user's interactions and views experienced via a HMD, including both the physical and virtual views as well as any additional injected content, may be live streamed to an external display for additional users to view the same experience.

As can be appreciated, the system described herein provides numerous benefits to a user or a physician. For example, using the augmented reality system for spine surgery, or for any other surgical procedure, allows the surgeon to better prepare for the surgery and perform surgery in a safer manner. This is made possible because of the unique and novel view presented to the surgeon which allows the surgeon to view a combination of bone and anatomy including soft tissue, nerves, spine, blood vessels, lungs, etc. and to view an anatomy even if it is obscured by other tissue.

Figure 9:
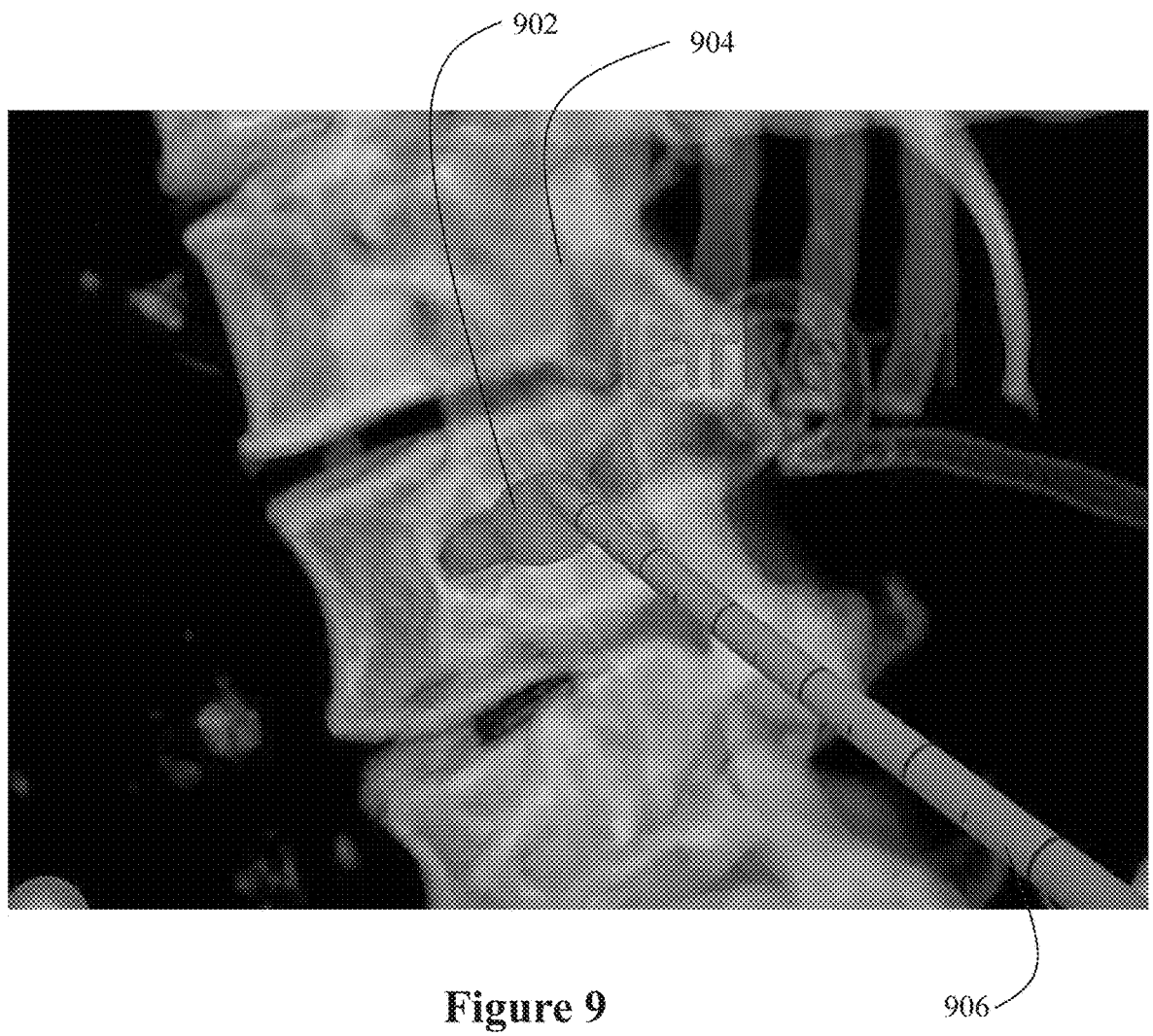
FIG. 9 illustrates an example system for augmented reality spine surgery.

In one example, as illustrated in FIG. 9, in order to help guide a physician with the placement of a screw, a physician (or any user) may place a virtual guide marker 902 within the anatomy represented by a virtual model 904. The virtual guide marker 902 enables the physician to plan for a spinal surgery, for example, by placing the guide marker 902 (which is indicative of a position and a direction) to indicate a location a screw is to be placed during surgery. In addition to planning for the surgical procedure, the guide marker 902 can then also be used during the surgical procedure to guide in the placement of the screw. When positioning the guide marker 902, the physician is able to adjust both the location as well as the angle or direction which a screw is to be inserted. A virtual probe 906 is used to simulate the approach, positioning, and placement of an actual probe with a screw (not shown).

Figure 10:
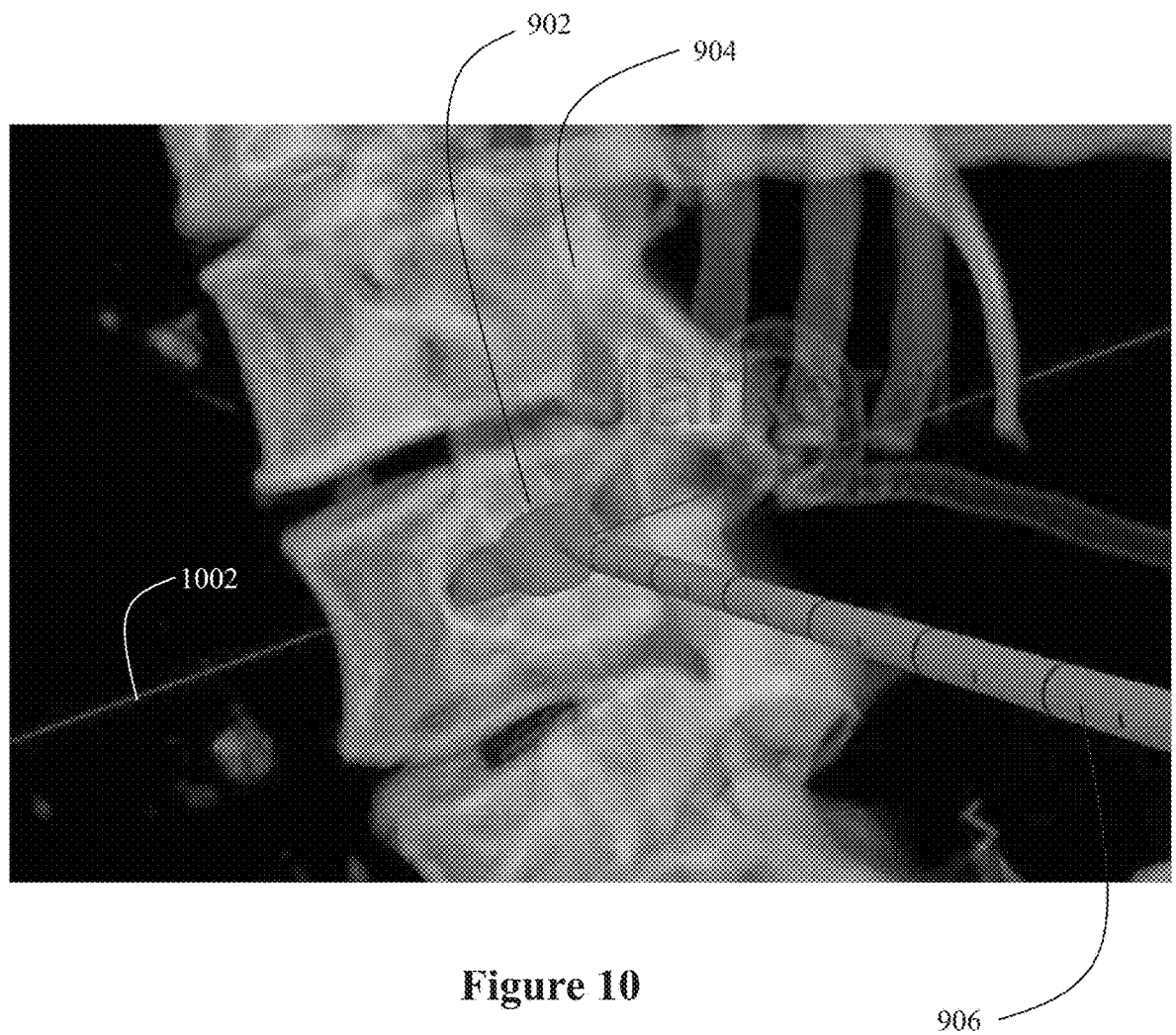
FIG. 10 illustrates an example system for augmented reality spine surgery.

In one example, as illustrated in FIG. 10, as the virtual probe 906 is brought closer to and approaches the guide marker 902, a distance between the virtual probe 906 and guide marker 902 is measured. Once the measured distance falls below a predetermined threshold level, meaning a proximity test has been passed, additional guide makers can be used to further refine placement of the virtual accessory. For the example provided in FIG. 10, a guide line 1002 appears in order to further guide the surgeon with the positioning of the virtual probe 906, such as by use of the physical probe with the physical model, and thereby better position the virtual screw in the desired position. In particular, the guide line 1002 will serve as an angle reference for guiding the angle at which the virtual probe 906 should be positioned. In one example, as the angle of the virtual probe 906 is adjusted with reference to the guide line 1002, the color of the at least one of or both of the guide line 1002 and the guide marker 902 may change colors to provide the physician with feedback and information as to the accuracy of the angle alignment. For example, when the virtual probe 906 is significantly misaligned with respect to the guide line 1002, the color may be red. As the virtual probe 906 moves closer into alignment with the guide line 1002 and the angle between the virtual probe 906 and the guide line 1002 drops below a predetermined threshold, the color may change to yellow. When the angle between the virtual probe 906 and the guide line 1002 drops below a second predetermined threshold, indicating the two are closely aligned, the color may change to green.

Figure 11:
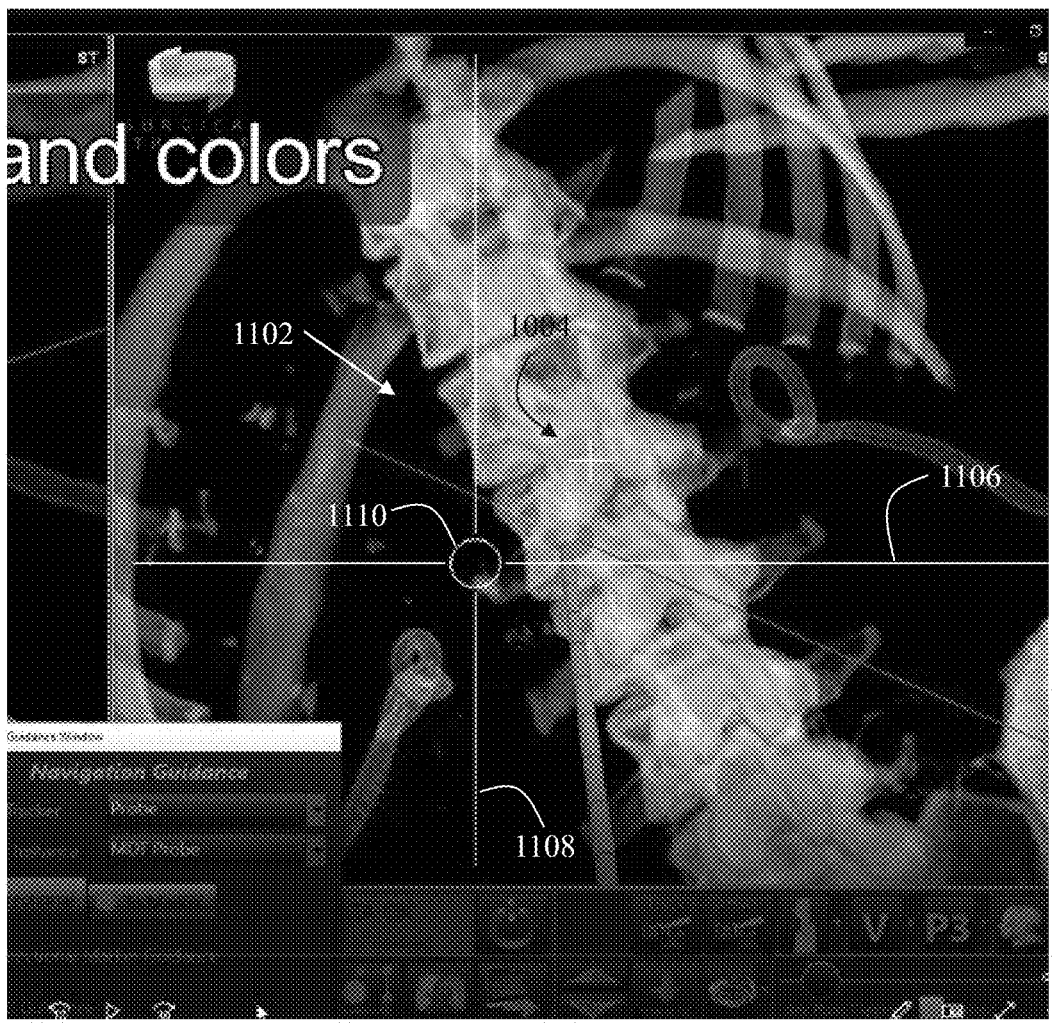
FIG. 11 illustrates an example system for augmented reality spine surgery.

In one example, as illustrated in FIG. 11, an guidance system, similar to an instrument landing system used to guide an aircraft to a runway ("ILS system") 1102 is used to further guide the physician to properly position the virtual probe 906 at the correct position and angle as the virtual probe 906 approaches a target 1104. The ILS system includes a horizontal guide 1106 and a vertical guide 1108, both of which bisect at a center point 1110. Using the visual guide of the ILS system 1102, the physician is able to adjust the virtual probe 906 by moving and tilting either in the vertical or horizontal direction and making corrections to the angle and position until the center point 1110 aligns with the target 1104. In one example, the ILS system 1102 functions in combination with the color feedback described in order to further guide the physician.

Figure 12:
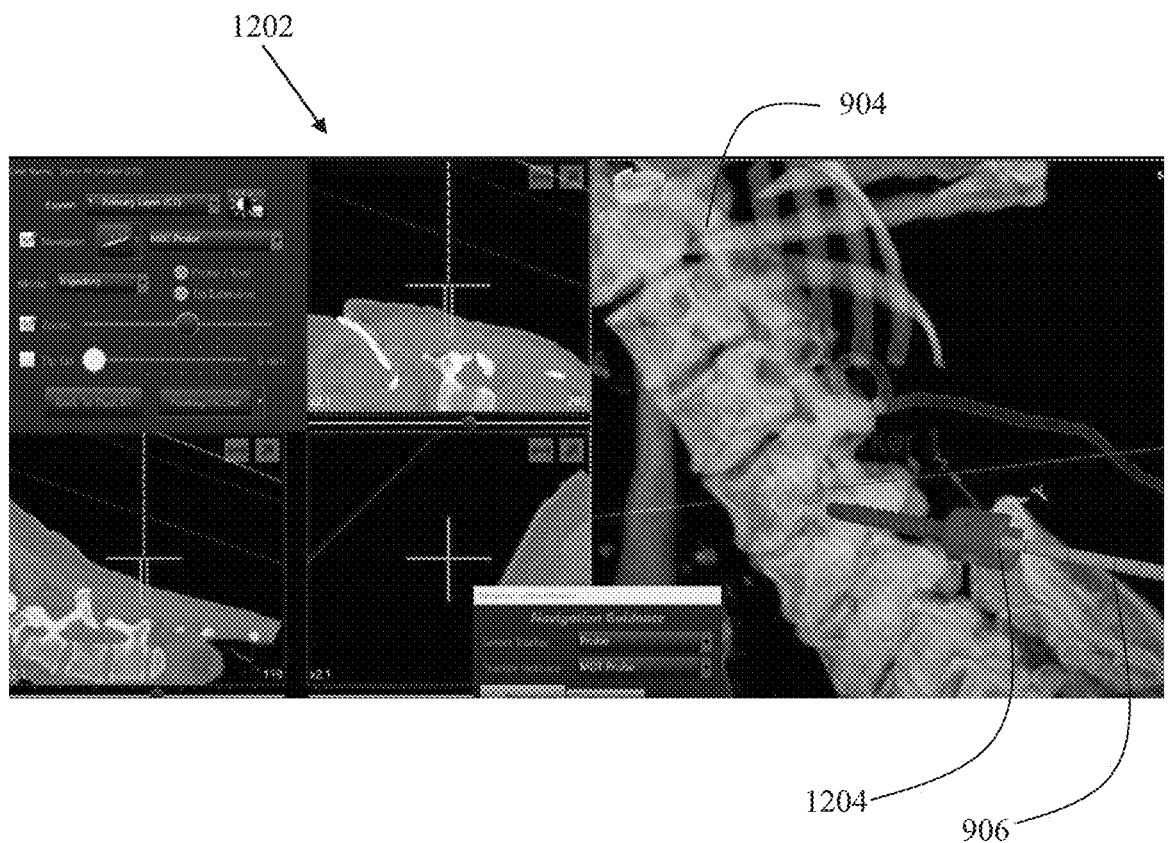
FIG. 12 illustrates an example system for augmented reality spine surgery.

In one example, as illustrated in FIG. 12, a DICOM representation 1202 corresponding to the virtual model 904 may be synchronized and tracked with the virtual model 904 and displayed alongside the view of the virtual model 904 in order to further aid the physician in visualizing and positioning of a virtual probe 906. In particular, as a physician, such as by using the physical probe brings the virtual probe 904 holding a screw 1204 within proximity of the virtual model 904 to simulate the placement of the screw 904, the position and direction of the virtual probe 904 and screw 1204 is simultaneously depicted in DICOM representation 1202 as well, thereby providing the physician with an additional perspective and guidance.

It should be appreciated that although references have been made to the guidance and positioning of a virtual probe 906 for simulation and preparation for surgery, the systems and methods described herein may similarly be used during an actual surgical procedure for guiding and positioning an actual physical probe and any desired implantable accessory within an actual anatomy, such as of a particular patient.

Figure 13:
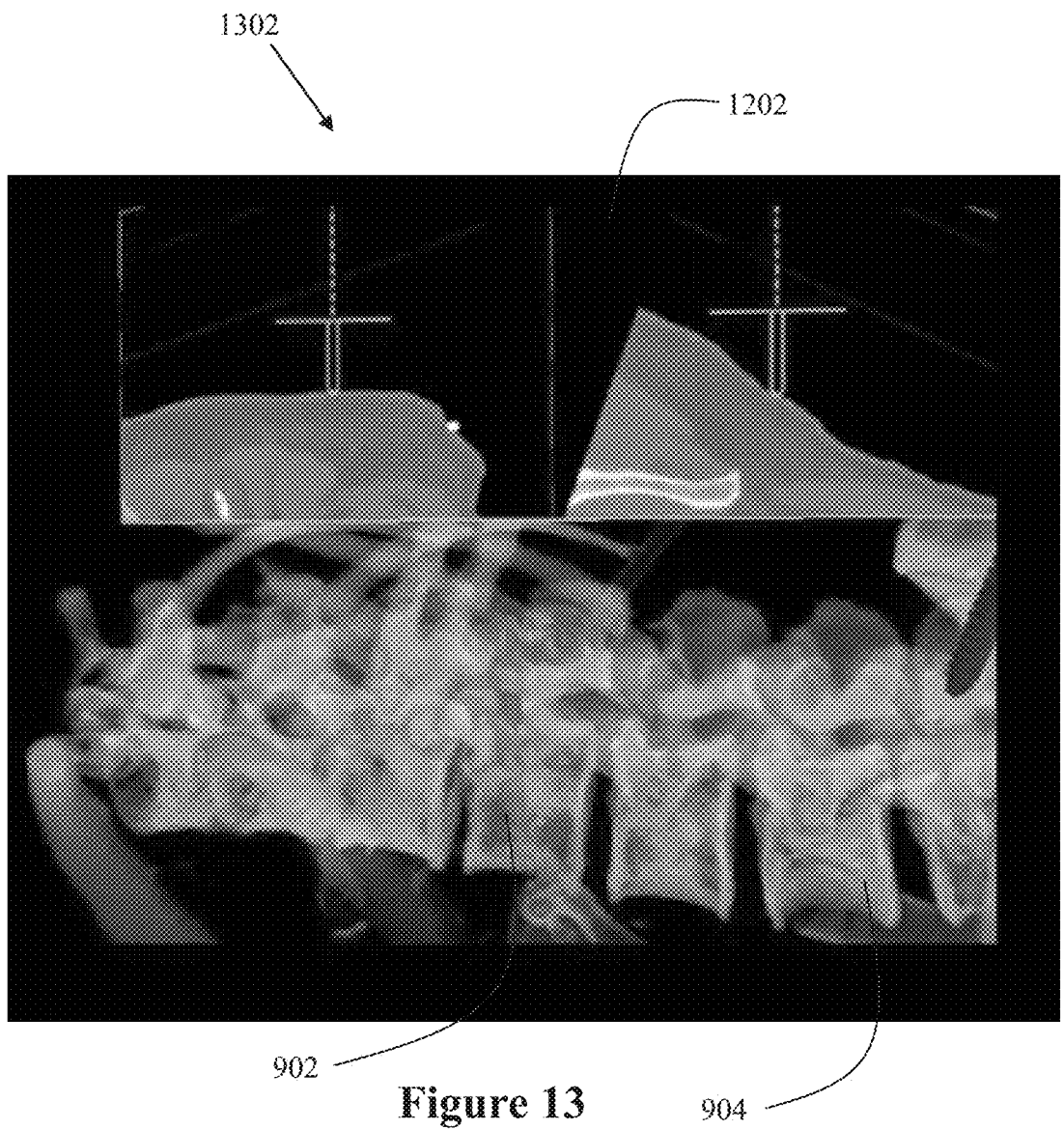
FIG. 13 illustrates an example system for augmented reality spine surgery.

It should be further appreciated that the virtual guide marker and the system and methods for guiding the positioning of a virtual or actual tool along with a virtual or actuals screw can be communicated and presented to a physician using a any suitable display device such a monitor or a HMD. In one example, as illustrated in FIG. 13, and HDM is used to present an augmented reality view 1302 including a guide marker 904 positioned on a virtual model 906 of an anatomy, both of which are overlayed in AR on top of a corresponding physical anatomy, as well as the corresponding DICOM 1202 positioned or floating near the view of the anatomy, also in AR, showing another view of the same anatomy and marker.

Figure 6:
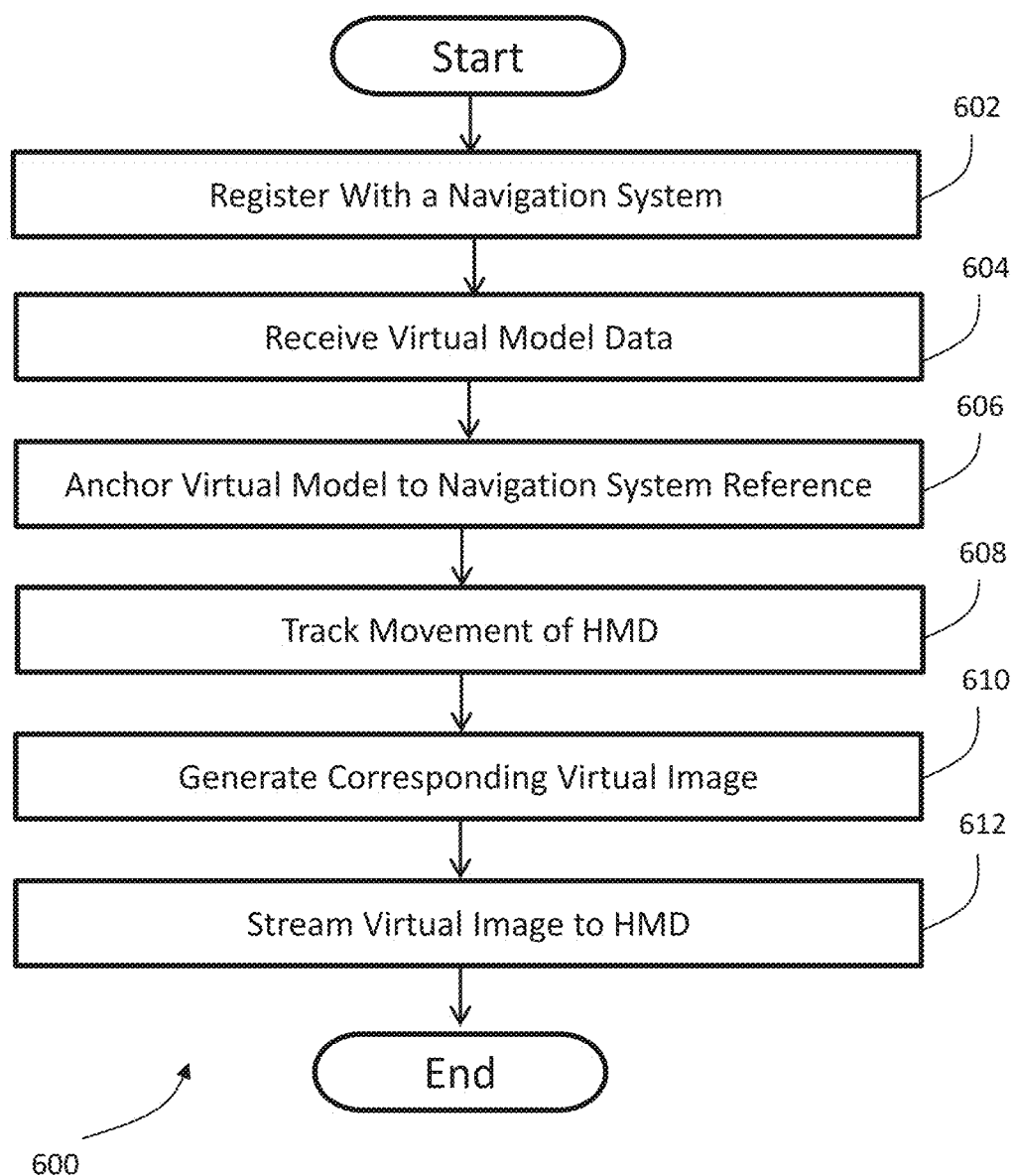
FIG. 6 illustrates an example method for augmenting and synchronizing a virtual model with a physical model.

FIG. 6 illustrates an example method for synchronizing and augmenting a virtual model with a physical model. At 602, the AR synchronization computer 112 receives synchronization and navigation data 120 from the navigation system 118 and registers the HMD 110 with the navigation system 118. At 604, the AR synchronization computer 112 receives data representative of a virtual model 102 from the virtual model database 114. At 606, the AR synchronization computer 112 anchors the virtual model 102 to the navigation system 118 reference. At 608, the AR synchronization computer 112 receives tracking data indicative of movement of the HMD 110. In one example, the tracking data is received from the navigation system 118. In another example, the tracking data is received from the HMD 110. At 610, the AR synchronization computer 112 renders the virtual image 116 from the virtual model 102 based on the received tracking data. At 612, the AR synchronization computer 112 streams the virtual image 116 to the HMD 110 in order to generate the augmented realty view 108 of the physical model 104.

Figure 7:
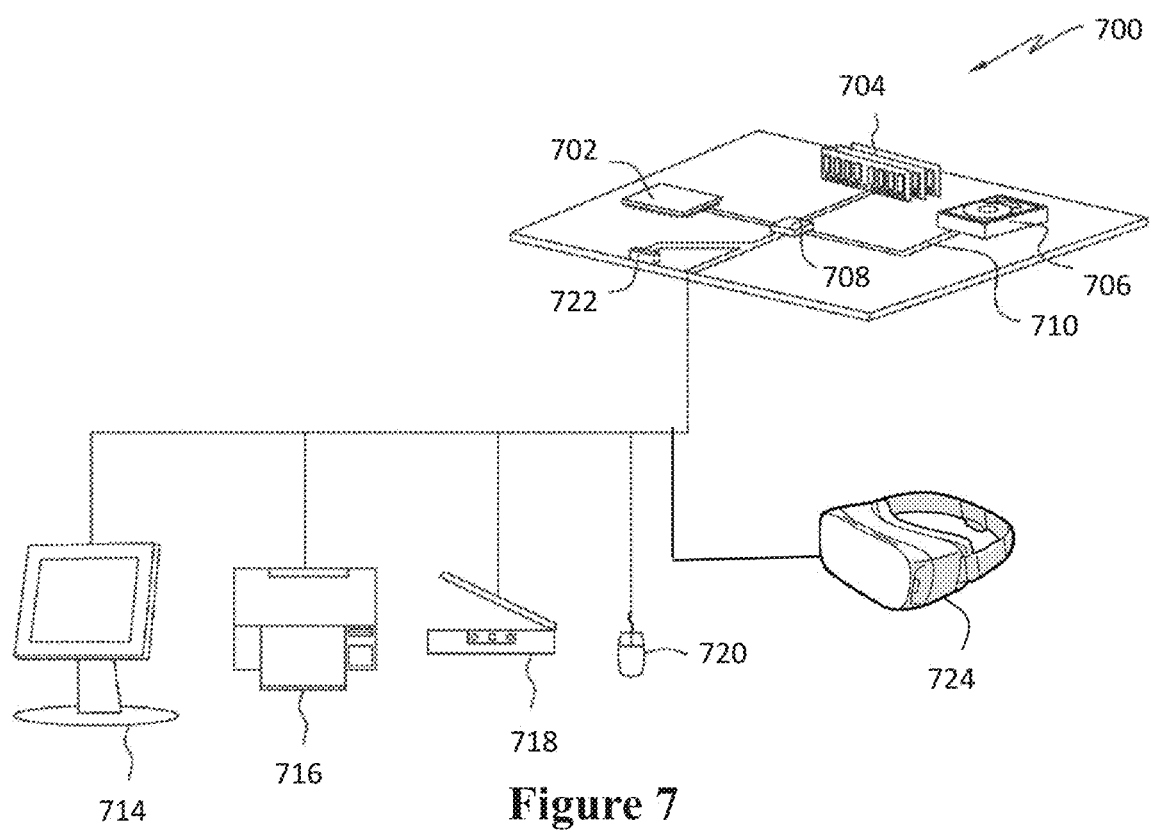
FIG. 7 illustrates an example computer implementing the example augmented reality synchronization computer of FIG. 1.

FIG. 7 is a schematic diagram of an example computer for implementing the AR synchronization computer 112 of FIG. 1. The example computer 700 is intended to represent various forms of digital computers, including laptops, desktops, handheld computers, tablet computers, smartphones, servers, and other similar types of computing devices. Computer 700 includes a processor 702, memory 704, a storage device 706, and a communication port 708, operably connected by an interface 710 via a bus 712.

Processor 702 processes instructions, via memory 704, for execution within computer 600. In an example embodiment, multiple processors along with multiple memories may be used.

Memory 704 may be volatile memory or non-volatile memory. Memory 704 may be a computer-readable medium, such as a magnetic disk or optical disk. Storage device 706 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 704 or storage device 706.

Computer 700 can be coupled to one or more input and output devices such as a display 714, a printer 716, a scanner 718, a mouse 720, and a HMD 724.

As will be appreciated by one of skill in the art, the example embodiments may be actualized as, or may generally utilize, a method, system, computer program product, or a combination of the foregoing. Accordingly, any of the embodiments may take the form of specialized software comprising executable instructions stored in a storage device for execution on computer hardware, where the software can be stored on a computer-usable storage medium having computer-usable program code embodied in the medium.

Databases may be implemented using commercially available computer applications, such as open source solutions such as MySQL, or closed solutions like Microsoft SQL that may operate on the disclosed servers or on additional computer servers. Databases may utilize relational or object oriented paradigms for storing data, models, and model parameters that are used for the example embodiments disclosed above. Such databases may be customized using known database programming techniques for specialized applicability as disclosed herein.

Any suitable computer usable (computer readable) medium may be utilized for storing the software comprising the executable instructions. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet.

In the context of this document, a computer usable or computer readable medium may be any medium that can contain, store, communicate, propagate, or transport the program instructions for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, local communication busses, radio frequency (RF) or other means.

Computer program code having executable instructions for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, C #, Object Pascal, or the like, artificial intelligence languages such as Prolog, a real-time embedded language such as Ada, or even more direct or simplified programming using ladder logic, an Assembler language, or directly programming using an appropriate machine language.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

The invention claimed is:

1. A method for using a computer system for rendering an interactive augmented view of a physical model representing an anatomical feature and virtual accessory model of an implantable surgical accessary, said method comprising the steps of:
   storing data representing the implantable surgical accessory in a database;
   providing a physical probe configured for use by a user to interact with the physical model:
   the computer system being configured for generating the virtual accessory model of the implantable surgical accessory utilizing the data representing the implantable surgical accessory;
   the computer system being configured for determining a direction of view of the user;
   the computer system being configured for tracking a position of the physical probe about the physical model;
   the computer system being configured for generating an image of the physical model based on the determined direction of view of the user;
   the computer system being configured for generating an image of the surgical probe based on the tracked position of the physical probe;
   the computer system being configured for generating and displaying an augmented reality view to the user, said augmented reality view showing realistic interaction of the virtual accessory model with the generated image of the physical probe and the generated image of the physical model such that the user can realistically manipulate the virtual accessory model based on user interactions with the physical probe about the physical model;
   the computer system being configured to display in the augmented reality view a guide marker on the image of the physical model to guide the user in maneuvering the physical probe to a desired placement of the virtual accessory model with respect to the physical model; and
   the computer system being configured to perform a proximity test on the virtual probe to detect a distance between the virtual probe and the guide marker as the virtual probe is brought closer to the guide marker, and, upon detecting the distance falling below a predetermined threshold level, displaying in the augmented reality view a guide line in addition to the guide marker that is otherwise not visible prior to virtual probe being within the predetermined threshold of level of the guide marker, wherein the guide line is utilized to refine guidance and placement of the virtual accessory into the desired location.

2. The method of claim 1, wherein said implantable surgical accessory is an implantable screw.

3. The method of claim 2, wherein said physical model includes one or more portions of a skeleton.

4. The method of claim 2, wherein said implantable screw is an actual surgical screw commercially available for use in medical procedures.

5. The method of claim 1, further comprising the step of the computer system providing a plurality of additional virtual models selectable by the user using a user interface to the computer system, wherein said augmented reality view includes interactions with a selected one of the additional virtual models.

6. The method of claim 5, wherein the selected one of the virtual models provides one or more additional anatomical features overlaid upon the image of the physical model.

7. The method of claim 6, wherein the one or more additional anatomical features overlaid upon the image of the physical model are based on actual anatomical features of an actual patient.

8. The method of claim 5, further comprising the step of the computer system being configured to display in the augmented reality view one or more guide markers on the image of the physical model or the image of selected one of the additional virtual models to guide the user in maneuvering the physical probe to a desired placement of the virtual accessory model with respect to the respective one of the physical model or the selected one of the additional virtual models.

9. The method of claim 1, wherein the physical model is based on actual anatomical features of an actual patient.

10. The method of claim 1, wherein said guide line serve as an angle reference and/or color code for guiding the angle at which the physical probe should be positioned.

11. A method for using a computer system for rendering an interactive augmented view of a physical model representing an anatomical feature and virtual accessory model of a commercially available implantable surgical accessary, said method comprising the steps of:
   storing data representing the implantable surgical accessory in a database;
   providing a physical probe configured for use by a user to interact with the physical model;
   the computer system being configured for generating the virtual accessory model of the implantable surgical accessory utilizing the data representing the implantable surgical accessory;
   the computer system being configured for determining a direction of view of the user;
   the computer system being configured for tracking a position of the physical probe about the physical model;
   the computer system being configured for generating an image of the physical model based on the determined direction of view of the user;
   the computer system being configured for generating an image of the surgical probe based on the tracked position of the physical probe;

the computer system being configured for generating and displaying an augmented reality view to the user, said augmented reality view showing realistic interaction of the virtual accessory model with the generated image of the physical probe and the generated image of the physical model such that the user can realistically manipulate the virtual accessory model based on user interactions with the physical probe about the physical model;

the computer system being configured for displaying, in the augmented reality view, one or more guide markers on the image of the physical model to guide the user in maneuvering the physical probe to a desired placement of the virtual accessory model with respect to the physical model;

the computer system being configured to display in the augmented reality view a guide marker on the image of the physical model to guide the user in maneuvering the physical probe to a desired placement of the virtual accessory model with respect to the physical model; and the computer system being configured to perform a proximity test on the virtual probe to detect a distance between the virtual probe and the guide marker as the virtual probe is brought closer to the guide marker, and, upon detecting the distance falling below a predetermined threshold level, displaying in the augmented reality view a guide line in addition to the guide marker that is otherwise not visible prior to virtual probe being within the predetermined threshold of level of the guide marker, wherein the guide line is utilized to refine guidance and placement of the virtual accessory into the desired location.

12. The method of claim 11, wherein said implantable surgical accessory is an implantable screw.

13. The method of claim 12, wherein said physical model includes one or more portions of a skeleton.

14. The method of claim 12, wherein said implantable screw is an actual surgical screw commercially available for use in medical procedures.

15. The method of claim 11, further comprising the step of the computer system being configured for providing a plurality of additional virtual models selectable by the user using a user interface to the computer system, wherein said augmented reality view includes interactions with a selected one of the additional virtual models.

16. The method of claim 15, wherein the selected one of the virtual models provides one or more additional anatomical features overlaid upon the image of the physical model.

17. The method of claim 16, wherein the one or more additional anatomical features overlaid upon the image of the physical model are based on actual anatomical features of an actual patient.

18. The method of claim 11, wherein the physical model is based on actual anatomical features of an actual patient.

19. The method of claim 11, wherein said guide line serve as an angle reference for guiding the angle at which the physical probe should be positioned.

20. The method of claim 11, wherein said one or more guide markers serve as an angle reference for guiding the angle at which the physical probe should be positioned.

21. The method of claim 11, wherein said one or more guide markers utilize color for guiding the positioning of the physical probe.

22. A method for using a computer system for rendering an interactive augmented view of a physical model including at least part of a skeleton and a virtual screw model of a commercially available implantable screw, said method comprising the steps of:

storing data representing the implantable screw in a database;

providing a physical probe configured for use by a user to interact with the physical model;

the computer system being configured for generating the virtual screw model of the implantable screw utilizing the data representing the implantable screw;

the computer system being configured for determining a direction of view of the user;

the computer system being configured for tracking a position of the physical probe about the physical model;

the computer system being configured for generating an image of the physical model based on the determined direction of view of the user;

the computer system being configured for generating an image of the surgical probe based on the tracked position of the physical probe;

the computer system being configured for generating and displaying an augmented reality view to the user, said augmented reality view showing realistic interaction of the screw model with the generated image of the physical probe and the generated image of the physical model such that the user can realistically manipulate the screw model based on user interactions with the physical probe about the physical model to interact with the part of the skeleton;

the computer system being configured for displaying, in the augmented reality view, one or more guide markers on the image of the physical model to guide the user in maneuvering the physical probe to a desired placement of the screw model with respect to the part of the skeleton; and the computer system being configured to perform a proximity test on the virtual probe to detect a distance between the virtual probe and the guide marker as the virtual probe is brought closer to the guide marker, and, upon detecting the distance falling below a predetermined threshold level, displaying in the augmented reality view a guide line in addition to the guide marker that is otherwise not visible prior to virtual probe being within the predetermined threshold of level of the guide marker, wherein the guide line is utilized to refine guidance and placement of the virtual accessory into the desired location.

23. A method for using a computer system for rendering an interactive augmented view of a physical model representing an anatomical feature and virtual accessory model of a commercially available implantable surgical accessary, said method comprising the steps of:

storing data representing the implantable surgical accessory in a database;

providing a physical probe configured for use by a user to interact with the physical model;

the computer system being configured for generating the virtual accessory model of the implantable surgical accessory utilizing the data representing the implantable surgical accessory;

the computer system being configured for determining a direction of view of the user;

the computer system being configured for tracking a position of the physical probe about the physical model;

the computer system being configured for generating a virtual model of the physical model based on the determined direction of view of the user and desired features of the virtual model of the physical model stored in the database;

the computer system being configured for generating a virtual model of the surgical probe based on the tracked position of the physical probe and desired features of the virtual model of the physical probe stored in the database;

the computer system being configured for generating and displaying an augmented reality view to the user, said augmented reality view showing realistic interaction of the virtual accessory model with the virtual model of the physical probe and the virtual model of the physical model such that the user can realistically manipulate the virtual accessory model based on user interactions with the physical probe about the physical model;

the computer system being configured for displaying, in the augmented reality view, one or more guide markers on the virtual model of the physical model to guide the user in maneuvering the physical probe to a desired placement of the virtual accessory model with respect to the virtual model of the physical model; and the computer system being configured to perform a proximity test on the virtual probe to detect a distance between the virtual probe and the guide marker as the virtual probe is brought closer to the guide marker, and, upon detecting the distance falling below a predetermined threshold level, displaying in the augmented reality view a guide line in addition to the guide marker that is otherwise not visible prior to virtual probe being within the predetermined threshold of level of the guide marker, wherein the guide line is utilized to refine guidance and placement of the virtual accessory into the desired location.

* * * * *